(12) United States Patent
Takahashi et al.

(10) Patent No.: US 12,023,009 B2
(45) Date of Patent: Jul. 2, 2024

(54) ENDOSCOPE REPROCESSOR

(71) Applicant: OLYMPUS CORPORATION, Tokyo (JP)

(72) Inventors: Keigo Takahashi, Musashino (JP); Atsushi Kinoshima, Higashiyamato (JP); Kei Kimura, Hachioji (JP); Yuta Kameda, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 422 days.

(21) Appl. No.: 17/521,182

(22) Filed: Nov. 8, 2021

(65) Prior Publication Data

US 2022/0053999 A1 Feb. 24, 2022

Related U.S. Application Data

(63) Continuation of application No. PCT/JP2019/019731, filed on May 17, 2019.

(51) Int. Cl.
*A61B 1/12* (2006.01)
*A61B 90/70* (2016.01)
*B08B 3/14* (2006.01)

(52) U.S. Cl.
CPC .............. *A61B 1/123* (2013.01); *B08B 3/14* (2013.01); *A61B 2090/701* (2016.02)

(58) Field of Classification Search
CPC ........................................ A61B 1/123
See application file for complete search history.

(56) References Cited

U.S. PATENT DOCUMENTS

2016/0249794 A1   9/2016  Suzuki

FOREIGN PATENT DOCUMENTS

| JP | 10-234646 A | 9/1998 |
|---|---|---|
| JP | 2009-100939 A | 5/2009 |
| JP | 4905443 B2 | 3/2012 |
| JP | 2014-212821 A | 11/2014 |
| JP | 5885894 B1 | 3/2016 |
| JP | 2017-42532 A | 3/2017 |
| JP | 6178977 A2 | 8/2017 |
| JP | 6219010 A2 | 10/2017 |
| WO | 2015/198696 A1 | 12/2015 |

OTHER PUBLICATIONS

International Search Report dated Jul. 30, 2019 issued in PCT/JP2019/019731.

*Primary Examiner* — Spencer E. Bell
(74) *Attorney, Agent, or Firm* — Scully, Scott, Murphy & Presser, P.C.

(57) ABSTRACT

An endoscope reprocessor includes: a holding member to/from which a filtering tool is attachable and detachable; a fluid introduction conduit and a fluid discharge conduit that communicate with the filtering tool in a state in which the filtering tool is attached to the holding member; a moving member configured to, when the filtering tool is attached to the holding member and a weight of the filtering tool is less than a predetermined value, position the filtering tool in a first position and, when the filtering tool is attached to the holding member and the weight of the filtering tool is greater than or equal to the predetermined value, position the filtering tool in a second position that is different from the first position; and a hindering unit configured to, when the filtering tool is positioned in the second position, hinder removal of the filtering tool from the holding member.

5 Claims, 20 Drawing Sheets

ENDOSCOPE REPROCESSOR

CROSS REFERENCE TO RELATED APPLICATION

This application is a continuation application of PCT/JP2019/019731 filed on May 17, 2019, the entire contents of which are incorporated herein by this reference.

BACKGROUND OF THE INVENTION

1. Field of the Invention

The present invention relates to an endoscope reprocessor provided with a holding unit to/from which a filtering tool is attachable and detachable.

2. Description of the Related Art

An endoscope for medical use is subjected to reprocessing after use. An endoscope reprocessor has been known as a device configured to automatically carry out the reprocessing of endoscopes. The endoscope reprocessor is provided with a filtering tool including a filter configured to filter a liquid used for the reprocessing. Upon replacement of the filter, the entire filtering tool is removed from the endo scope reprocess or.

In a case of removing the filter from the endoscope reprocessor, it has been cumbersome to watch out for dripping from the filtering tool or a conduit connected to the filtering tool.

For example, Japanese Patent No. 4905443 discloses a washing machine that is provided with detection means configured to detect a liquid inside a space in which a filter is disposed, and, when the liquid is detected to be present, restrict removal of the filter.

SUMMARY OF THE INVENTION

An endoscope reprocessor according to one aspect of the present invention comprises: a holding member to/from which a filtering tool is attachable and detachable; a fluid introduction conduit and a fluid discharge conduit that communicate with the filtering tool in a state in which the filtering tool is attached to the holding member; a moving member configured to, when the filtering tool is attached to the holding member and a weight of the filtering tool is less than a predetermined value, position the filtering tool in a first position and, when the filtering tool is attached to the holding member and the weight of the filtering tool is greater than or equal to the predetermined value, position the filtering tool in a second position that is different from the first position; and a hindering unit configured to, when the filtering tool is positioned in the second position, hinder removal of the filtering tool from the holding member.

Another endoscope reprocessor according to one aspect of the present invention comprises: a holding member to/from which a filtering tool is attachable and detachable; a fluid introduction conduit and a fluid discharge conduit that communicate with the filtering tool in a state in which the filtering tool is attached to the holding member; a moving member configured to, when the filtering tool is attached to the holding member and a liquid is present in an amount less than a predetermined amount in the filtering tool, position the filtering tool in a first position and, when the filtering tool is attached to the holding member and the liquid is present in an amount greater than or equal to the predetermined amount in the filtering tool, position the filtering tool in a second position that is different from the first position; and a hindering unit configured to, when the filtering tool is positioned in the second position, hinder removal of the filtering tool from the holding member.

DETAILED DESCRIPTION OF THE PREFERRED EMBODIMENTS

Hereinafter, preferred embodiments of the present invention are described with reference to the drawings. Note that, in each of the figures used for the following description, constitutive elements may have different scales in order that each of the constitutive elements has a recognizable size on the figures, and the present invention is not limited to the number, shapes, ratios of size, and relative positional relationships of the constitutive elements featured in the figures.

First Embodiment

Figure 1:
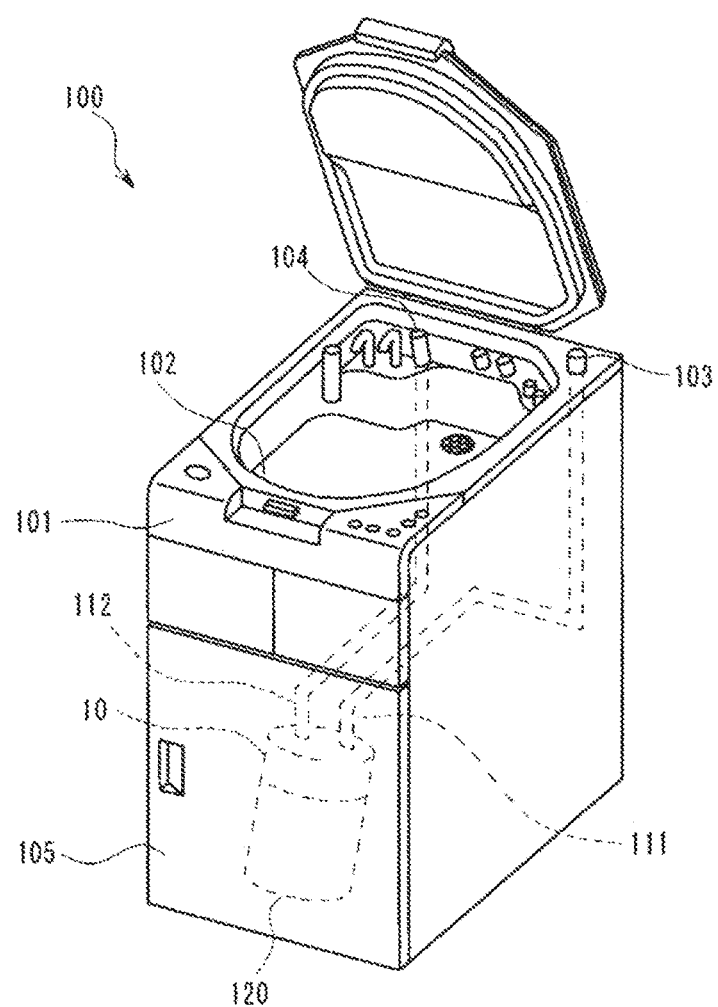
FIG. 1 is a perspective view of an endoscope reprocessor of a first embodiment.

Hereinafter, one example of the embodiments of the present invention is described. An endoscope reprocessor 100 shown in FIG. 1 is a device configured to subject at least one of an endoscope, an endoscope accessory, or a medical instrument to reprocessing. The reprocessing as referred to herein is not particularly limited and may be any one of: a process of rinsing with water; a cleaning process of removing dirt such as organic matters; a disinfection process of inactivating predetermined microorganisms; a sterilization process of removing or killing all microorganisms, and a combination of the foregoing.

In the following description, the term "upward" refers to a position more distant from the ground than a comparison target, and the term "downward" refers to a position closer to the ground than a comparison target. In other words, "downward" refers to the gravity direction. In the following description, the terms "high" and "low" represent a height relationship in the gravity direction.

The endoscope reprocessor 100 is provided with a treatment tank 102. The treatment tank 102 has a concave shape with an opening portion, inside which at least one of an endoscope, an endoscope accessory, or a medical instrument can be placed. The treatment tank 102 is open upward, on an upper face of a reprocessor main body 101. The endoscope reprocessor 100 subjects at least one of the endoscope, the endoscope accessory, or the medical instrument to the reprocessing inside the treatment tank 102. The endoscope reprocessor 100 includes a configuration of introducing a fluid such as water and a medicinal solution used for the reprocessing.

A replaceable filtering tool 120 can be arranged inside the reprocessor main body 101. As described later in detail, the filtering tool 120 is a device configured to filter the liquid used for the reprocessing.

The reprocessor main body 101 includes a holding unit 10, a fluid introduction conduit 111, and a fluid discharge conduit 112.

The filtering tool 120 is attachable and detachable to/from the holding unit 10. The fluid introduction conduit 111 and the fluid discharge conduit 112 communicate with the filtering tool 120 in a state in which the filtering tool 120 is attached to the holding unit 10.

The fluid introduction conduit 111 introduces a fluid into the filtering tool 120. The fluid discharge conduit 112 discharges a liquid having been filtered by the filtering tool 120 from the filtering tool 120.

In the present embodiment, the filtering tool 120 filters water, as an example. In the present embodiment, water is supplied from a water facility provided outside the endoscope reprocessor 100, as an example. The reprocessor main body 101 is provided with a water introduction connector 103 that connects the fluid introduction conduit 111 to the water facility. A nozzle 104 configured to discharge water is provided inside the treatment tank 102.

In the state in which the filtering tool 120 is attached to the holding unit 10, the fluid introduction conduit 111 communicates between the water introduction connector 103 and the filtering tool 120, and the fluid discharge conduit 112 communicates between the filtering tool 120 and the nozzle 104. Consequently, in the present embodiment, water supplied from the water facility to the endoscope reprocessor 100 is filtered by the filtering tool 120 and then introduced into the treatment tank 102. Although not illustrated, the fluid introduction conduit 111 and the fluid discharge conduit 112 are each provided with a valve configured to control water flow. In the present embodiment, the fluid discharge conduit 112 communicates with the nozzle 104. However, the present invention is not limited to such a configuration, and the fluid discharge conduit 112 may also communicate with a tank configured to retain a medicinal solution.

The liquid filtered by the filtering tool 120 is not limited to water, and may also be a disinfectant solution and the like used for the reprocessing. The liquid filtered by the filtering tool 120 is not limited to a mode of being supplied from outside of the endoscope reprocessor 100, and may be retained in a tank provided inside the reprocessor main body 101.

In the present embodiment, a door 105 is provided on a lateral face of the reprocessor main body 101, as an example. When the door 105 is opened, an internal space of the reprocessor main body 101 is exposed to the outside. A user carries out a replacement operation of the filtering tool 120 in the state in which the door 105 is opened.

The endoscope reprocessor 100 has configurations of introducing a fluid such as a liquid or a gas other than water used for the reprocessing into the treatment tank 102. However, the configurations are similar to the well-known configurations and a detailed description of the configurations is omitted.

Next, a configuration of a filtering tool holding device 1 configured to arrange the filtering tool 120 inside the reprocessor main body 101 is described.

Figure 2:
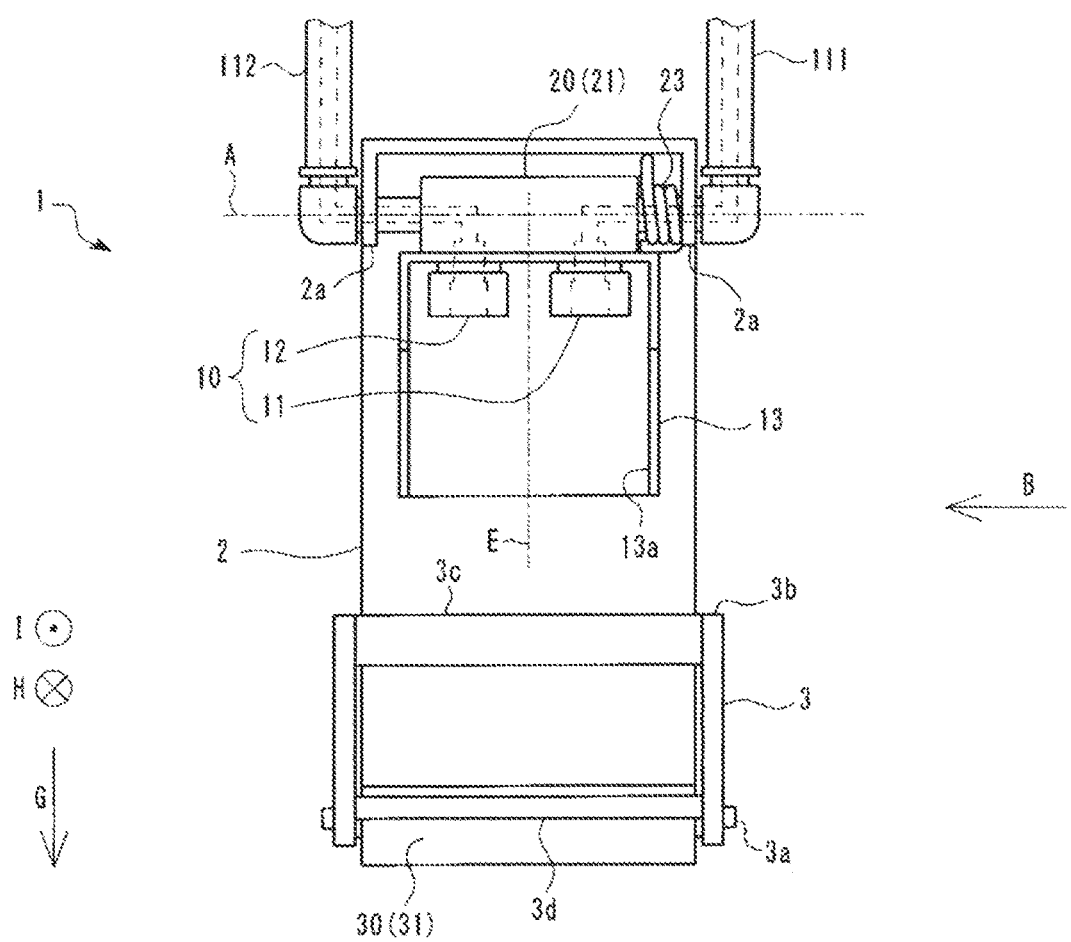
FIG. 2 is a front view of a filtering tool holding device of the first embodiment.
Figure 3:
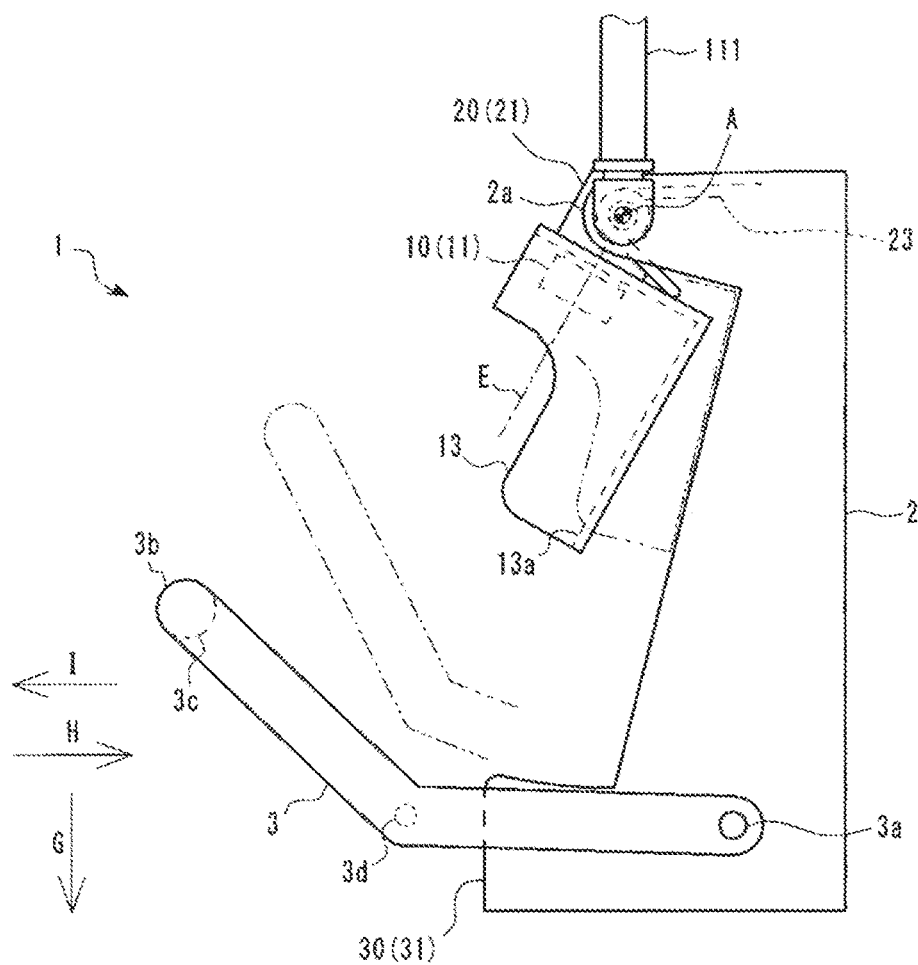
FIG. 3 is a lateral view of the filtering tool holding device of the first embodiment.
Figure 4:
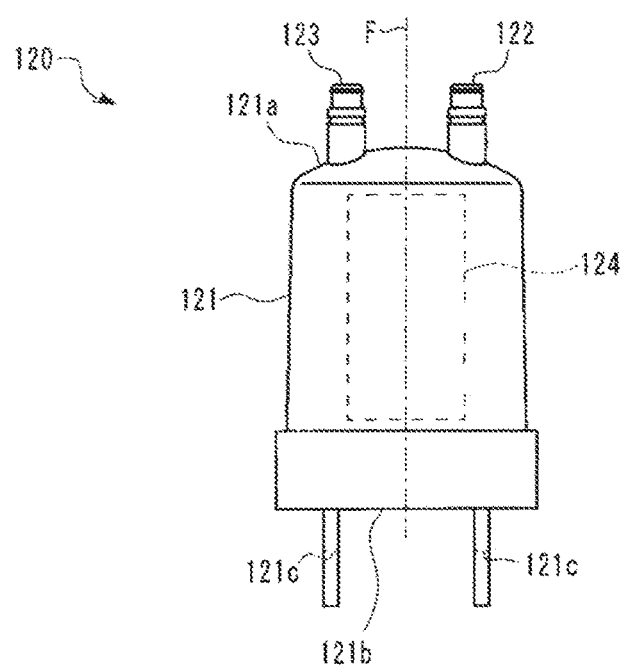
FIG. 4 is a front view of a filtering tool of the first embodiment.

FIG. 2 is a front view of the filtering tool holding device 1. FIG. 3 is a lateral view of the filtering tool holding device 1. FIG. 2 shows the filtering tool holding device 1 viewed from the outside of the reprocessor main body 101 with the door 105 being opened. FIG. 3 shows the filtering tool holding device 1 viewed in a direction shown by an arrow B in FIG. 2. FIG. 4 is a front view of the filtering tool 120.

In FIG. 2 and FIG. 3, a lower direction in the figures (direction shown by an arrow G) is downward (gravity direction). In FIG. 2, a direction from the top face to the reverse face of the sheet along an axis perpendicular to the sheet (direction shown by an arrow H) is referred to as "depth direction", and a direction opposite to the depth direction (direction shown by an arrow I) is referred to as "frontward direction". When the inside of the reprocessor main body 101 is seen from the outside in the state in which the door 105 is opened, the depth direction substantially corresponds to a direction from the outside to the inside of the reprocessor main body 101.

The filtering tool holding device 1 includes a base 2, the holding unit 10, a moving unit 20, and a hindering unit 30.

The base 2 is fixed to the reprocessor main body 101. In the present embodiment illustrated in the figures, as an example, the base 2 is an independent member. However, the base 2 may also be a part of a member configuring a frame or the like of the reprocessor main body 101.

The filtering tool 120 is attachable and detachable to/from the holding unit 10. The holding unit 10 is provided with a first socket 11 and a second socket 12. The fluid introduction conduit 111 communicates with the first socket 11. The fluid discharge conduit 112 communicates with the second socket 12. A primary side plug 122 and a secondary side plug 123, which are described later, of the filtering tool 120 are insertable and removable into/from the first socket 11 and the second socket 12. Although the holding unit 10 is exemplified by the socket, the present invention is not limited to such a configuration and, as the holding unit 10, a pinch or a rubber tube having an opening diameter smaller than the diameter of the plug may also be used.

A configuration of the filtering tool 120 is described. As shown in FIG. 4, the filtering tool 120 is provided with a housing 121, the primary side plug 122, and the secondary side plug 123. The housing 121 is a hollow container. The housing 121 has a substantially columnar outer shape. A filter 124 configured to filter a liquid is disposed inside the housing 121.

The primary side plug 122 communicates with a primary side space inside the housing 121. The secondary side plug 123 communicates with a secondary side space inside the housing 121. Inside the housing 121, the primary side space and the secondary side space are separated by the filter 124. The space on the primary side of the filter 124 refers to a space in which a liquid prior to passing through the filter 124 flows, and the space on the secondary side of the filter refers to a space in which the liquid after passing through the filter 124 flows.

A combination of the first socket 11 and the primary side plug 122, and a combination of the second socket 12 and the secondary side plug 123 respectively configure joints of piping configured to let through a liquid. In the state in which the primary side plug 122 is inserted into the first socket 11, the fluid introduction conduit 111 communicates with a primary side space of the filtering tool 120. In the state in which the secondary side plug 123 is inserted into the second socket 12, the fluid discharge conduit 112 communicates with a secondary side space of the filtering tool 120.

In the present embodiment, the state in which the filtering tool 120 is attached to the holding unit 10 is a state in which the primary side plug 122 and the secondary side plug 123 are inserted into the first socket 11 and the second socket 12 respectively.

Note that, although a socket, which is a female connector, is provided on the holding unit 10, and a plug, which is a male connector, is provided on the filtering tool 120 as a configuration for connecting the holding unit 10 and the filtering tool 120 in the present embodiment, the gender of the members may be inverse.

The first socket 11 and the second socket 12 of the holding unit 10 are open in the same direction. In the present embodiment, the opening direction of the first socket 11 and the second socket 12 is parallel to a predetermined axis E fixed to the holding unit 10. The opening direction of the first socket 11 and the second socket 12 is substantially downward. Note that an angle of the axis E, and the opening direction of the first socket 11 and the second socket 12 are not limited to the angle and the opening direction of the present embodiment. For example, the axis E may be horizontal.

The primary side plug 122 and the secondary side plug 123 protrude from an upper face 121*a* of the housing 121 in the same direction. In the present embodiment, the primary side plug 122 and the secondary side plug 123 are cylindrical. The primary side plug 122 and the secondary side plug 123 extend in parallel to a predetermined axis F fixed to the housing 121. In the present embodiment, the axis F is a central axis of the housing 121 which is columnar.

Figure 5:
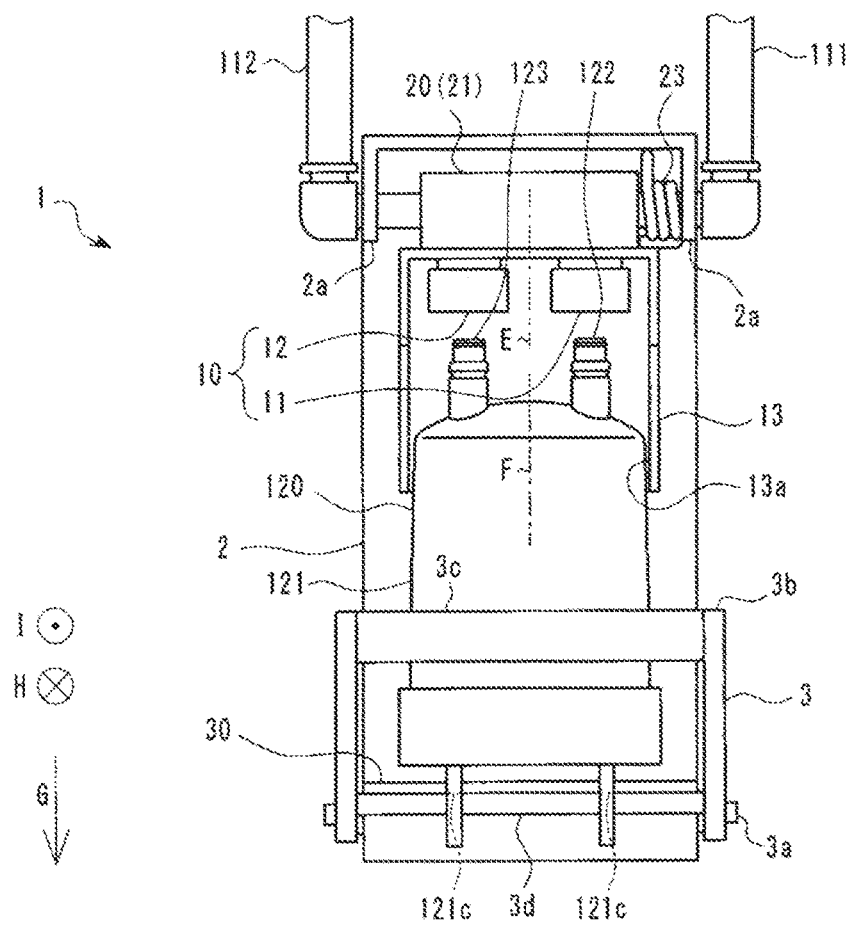
FIG. 5 shows a procedure of attaching the filtering tool to the filtering tool holding device of the first embodiment.
Figure 6:
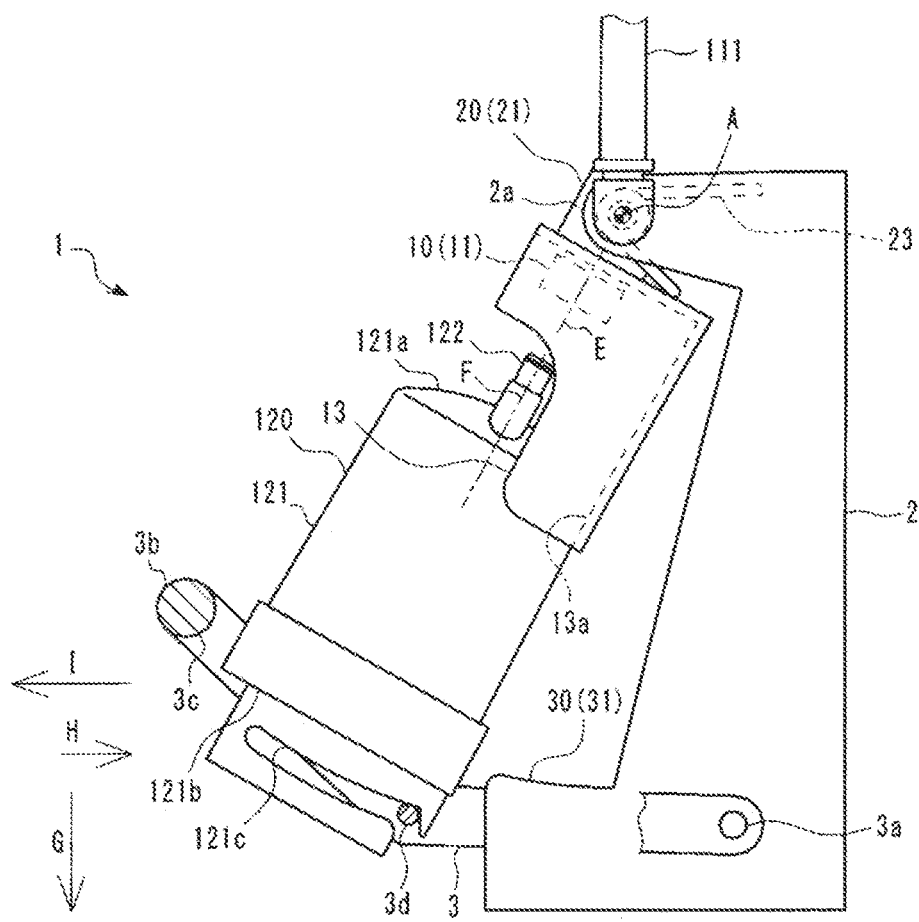
FIG. 6 shows a procedure of attaching the filtering tool to the filtering tool holding device of the first embodiment.

When attaching the filtering tool 120 to the holding unit 10 from the state in which the filtering tool 120 is removed from the holding unit 10, the user first orients the primary side plug 122 and the secondary side plug 123 to face the first socket 11 and the second socket 12 as shown in FIG. 5 and FIG. 6, and retains the axis F of the filtering tool 120 substantially parallel to the axis E of the holding unit 10. In the present embodiment, the first socket 11 and the second socket 12 are open substantially downward, and in such a state, the filtering tool 120 is in such an attitude that the upper face 121*a* of the housing 121 is directed upward.

Figure 7:
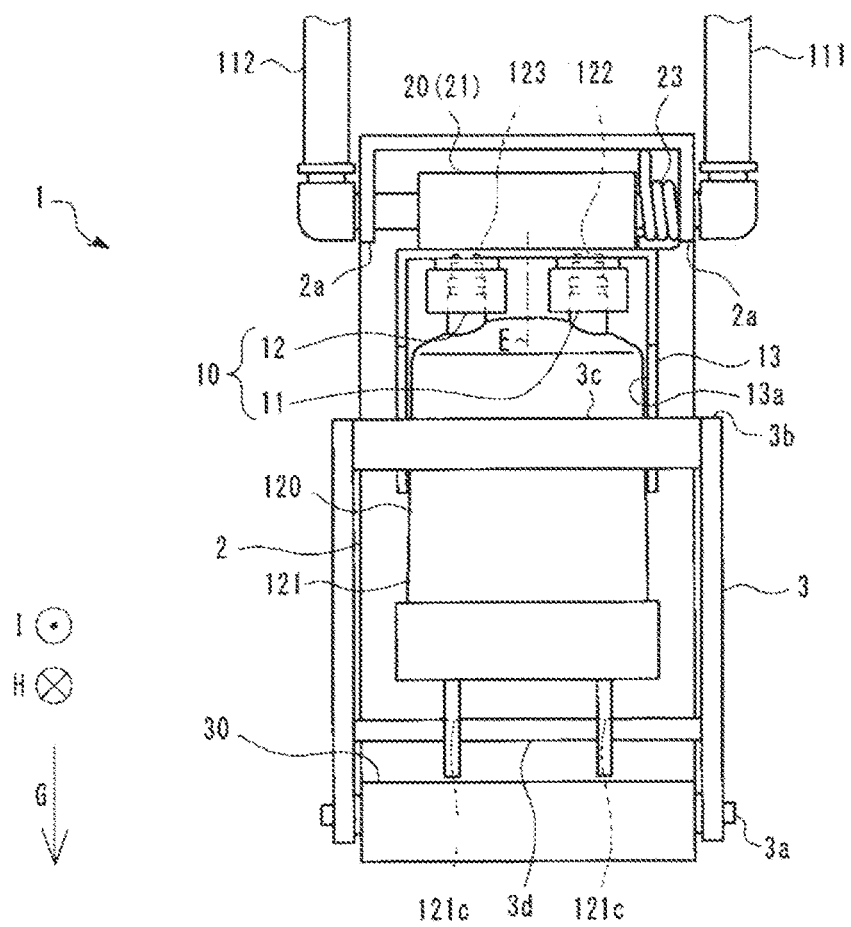
FIG. 7 shows a state in which the filtering tool is attached to the filtering tool holding device of the first embodiment.
Figure 8:
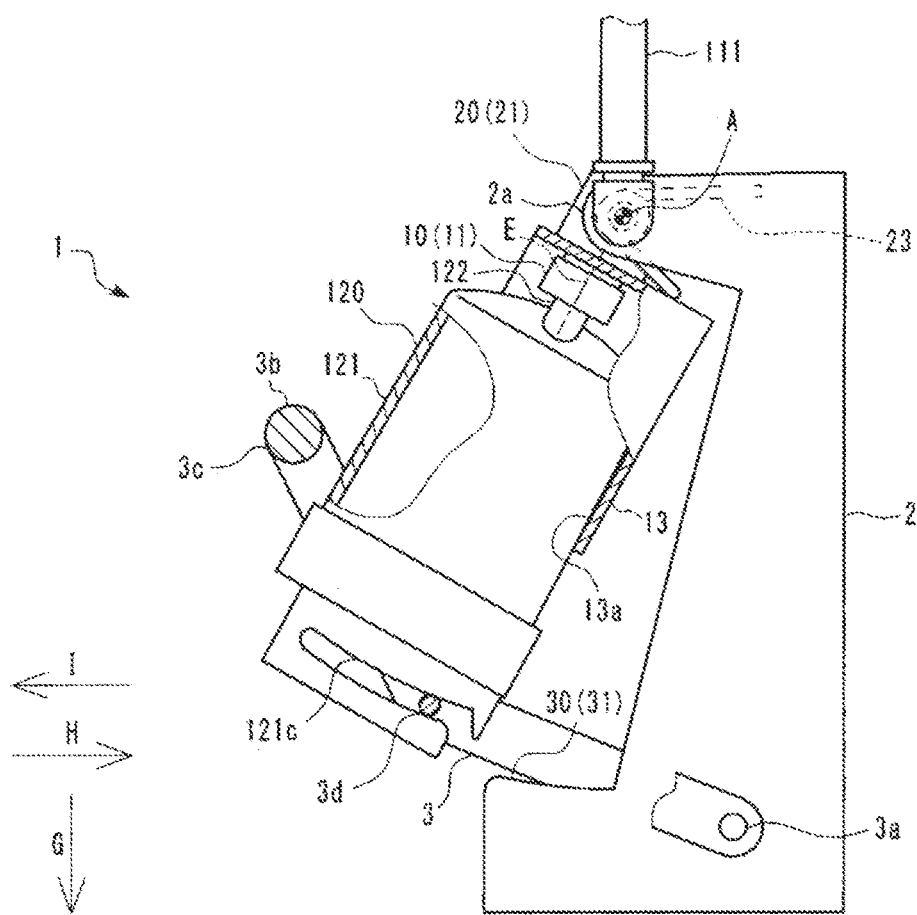
FIG. 8 shows a state in which the filtering tool is attached to the filtering tool holding device of the first embodiment and positioned in a first position.

Subsequently, when the user applies a force to the filtering tool 120 in a direction toward the holding unit 10 along the axis E, the primary side plug 122 and the secondary side plug 123 are inserted into the first socket 11 and the second socket 12 respectively, as shown in FIG. 7 and FIG. 8.

The holding unit 10 according to the present embodiment is provided with a guiding portion 13 configured to guide the position of the filtering tool 120 with respect to the holding unit 10 in a state in which the filtering tool 120 is removed from the holding unit 10. The guiding portion 13 is provided with a concave portion 13*a* extending along the axis E. When the housing 121 of the filtering tool 120 fits into the concave portion 13*a*, the axis F of the filtering tool 120 and the axis E of the holding unit 10 are substantially parallel. The filtering tool 120 is movable along the axis E with respect to the holding unit 10 in the state in which the housing 121 fits into the concave portion 13*a*.

In the state in which the filtering tool 120 is attached to the holding unit 10, when a force is applied to the filtering tool 120 along the axis E in a direction away from the holding unit 10 (the opening direction of the first socket 11 and the second socket 12), the filtering tool 120 is removed from the holding unit 10.

The filtering tool holding device 1 according to the present embodiment is provided with a lever 3, as an example. The lever 3 is a member that the user operates with fingers upon attachment and detachment of the filtering tool 120 to/from the holding unit 10. The force with which the user operates the lever 3 is converted by the lever 3 to a force moving the filtering tool 120 along the axis E.

More specifically, the lever 3 is swingable around a pivot point 3*a* provided on the base 2 as shown in FIG. 3. The pivot point 3*a* is provided downward and in the depth direction of the holding unit 10. The lever 3 extends from the pivot point 3*a* in the frontward direction. A distal end portion 3*b* of the lever 3 moves up and down in the vertical direction in association with the swinging of the lever 3 around the pivot point 3*a*.

The distal end portion 3*b* of the lever 3 is provided with a grasping portion 3*c* that the user grasps. An engaging portion 3*d* is provided between the distal end portion 3*b* and the pivot point 3*a* of the lever 3. As shown in FIG. 6, the engaging portion 3*d* engages with a hook 121*c* fixed to the housing 121 of the filtering tool 120.

The hook 121*c* is provided on a lower face 121*b* of the housing 121. When the lever 3 swings around the pivot point 3*a* in the state in which the engaging portion 3*d* engages with the hook 121*c*, the filtering tool 120 advances and retreats along the concave portion 13*b* in the guiding portion 13 substantially parallel to the axis E.

In other words, in the present embodiment, when the user lifts the grasping portion 3*c* of the lever 3 in the state shown in FIG. 5 and FIG. 6, the filtering tool 120 is attached to the holding unit 10 as shown in FIG. 7 and FIG. 8.

Note that it is not required that the filtering tool holding device 1 is provided with the lever 3. In such a case, the user grasps the housing 121 of the filtering tool 120 with a hand or a jig to attach and detach the filtering tool 120 to/from the holding unit 10 along the axis E.

Although not illustrated, the endoscope reprocessor 100 and the filtering tool 120 include a configuration of discharging a liquid present in the housing 121 to the outside of the housing 121. Although not illustrated, the endoscope reprocessor 100 and the filtering tool 120 include a configuration of discharging a liquid present in the fluid introduction conduit 111 to the outside of the fluid introduction conduit 111. When replacing the filtering tool 120, prior to removing the filtering tool 120 from the holding unit 10, the user needs to carry out a discharge operation of discharging a liquid present in the filtering tool 120 and the fluid introduction conduit 111. The discharge operation is referred to as, for example, water drainage.

The moving unit 20 moves the filtering tool 120 inside the reprocessor main body 101 according to the weight of the filtering tool 120. In particular, in the state in which the filtering tool 120 is attached to the holding unit 10, the moving unit 20 moves the filtering tool 120 relatively to the base 2 according to the weight of the filtering tool 120.

Here, the weight of the filtering tool 120 includes the weight of the liquid present in the housing 121. Therefore, in the case of the present embodiment, the weight of the filtering tool 120 varies according to the amount of water retained in the housing 121.

When the weight of the filtering tool 120 is less than a predetermined value, the moving unit 20 positions the filtering tool 120 in a first position with respect to the base 2. When the weight of the filtering tool 120 is greater than or equal to the predetermined value, the moving unit 20 positions the filtering tool 120 in a second position with respect to the base 2.

The predetermined value is less than the weight of the filtering tool 120 after use of the filtering tool 120 and prior to the discharging operation. The expression "after use of the filtering tool 120" means after the liquid flows from the fluid introduction conduit 111 to the fluid discharge conduit 112, via the filtering tool 120. In other words, after use of the filtering tool 120 and prior to the discharging operation, the liquid is present in the filtering tool 120 in such an amount that the housing 121 is filled with the liquid.

The predetermined value is greater than the weight of the filtering tool 120 after use of the filtering tool 120 and after the discharging operation. The predetermined value can be calculated on the basis of the weight of the filtering tool 120 in an unused state and a capacity of the housing 121.

In other words, when the filtering tool 120 after use and the discharging operation or the unused filtering tool 120 is attached to the holding unit 10, the moving unit 20 positions the filtering tool 120 in the first position. When the filtering tool 120 after use and prior to the discharging operation is attached to the holding unit 10, the moving unit 20 positions the filtering tool 120 in the second position.

A small amount of the liquid may be present in the filtering tool 120 after the discharging operation. However, an amount of change in the weight of the filtering tool 120 before and after the discharging operation after use is relatively great. In the present embodiment, the second position is lower than the first position. Then, the moving unit 20 leverages the change in the weight of the filtering tool 120 to move the filtering tool 120 with respect to the base 2.

A configuration by which the moving unit 20 leverages the change in the weight of the filtering tool 120 to move the filtering tool 120 with respect to the base 2 is not particularly limited. In the present embodiment, as an example, the moving unit 20 includes a swinging unit 21 configured to swing the holding unit 10 and the filtering tool 120 in the state of being attached to the holding unit 10 around a rotation axis A with respect to the base 2.

As shown in FIG. 2 and FIG. 3, the swinging unit 21 is supported in a swingable manner around the rotation axis A by a bearing 2a provided on the base 2. The rotation axis A is substantially horizontal. The holding unit 10 is fixed to the swinging unit 21. In the present embodiment, the guiding portion 13 is also fixed to the swinging unit 21.

Figure 9:
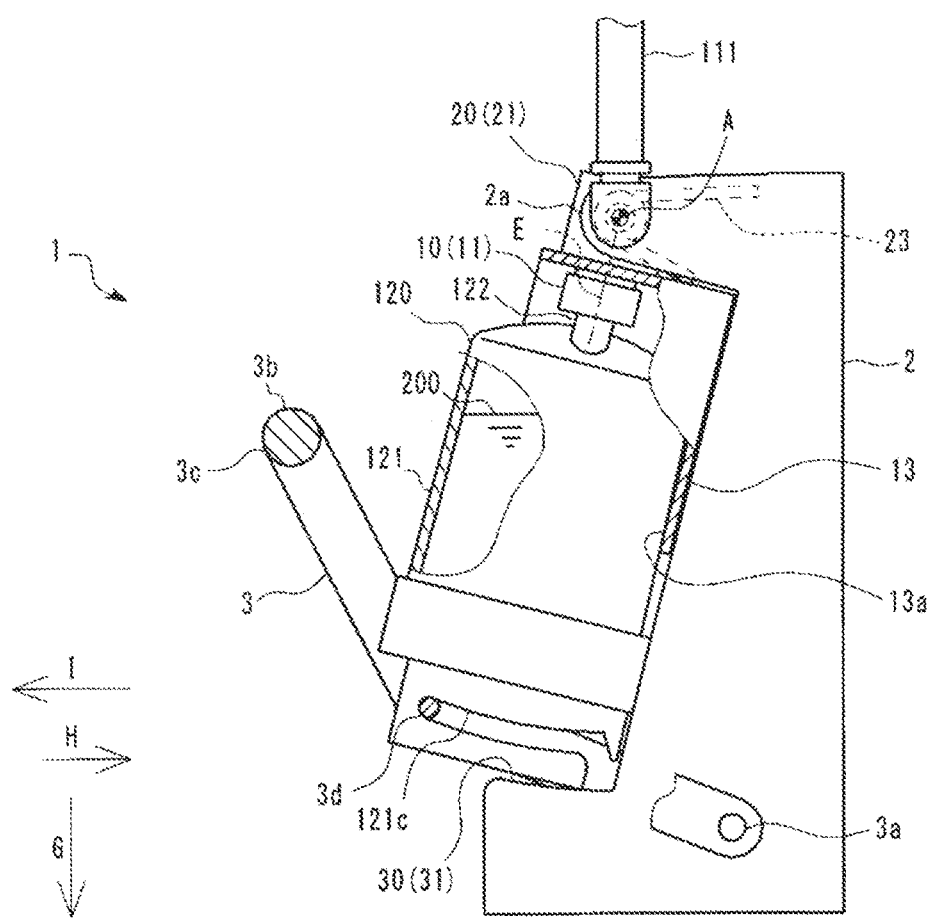
FIG. 9 shows a state in which the filtering tool is attached to the filtering tool holding device of the first embodiment and positioned in a second position.

In association with the swinging of the swinging unit 21, the filtering tool 120 attached to the holding unit 10 moves between the first position and the second position. FIG. 8 shows the state in which the filtering tool 120 is positioned in the first position, and FIG. 9 shows a state in which a liquid 200 is present in the filtering tool 120 and the filtering tool 120 is positioned in the second position.

The moving unit 20 includes an urging unit 23 configured to generate an urging force moving the filtering tool 120 in a direction from the second position to the first position. The urging force generated by the urging unit 23 is applied in a direction of lifting the filtering tool 120 upward against the gravity.

The urging force generated by the urging unit 23 has such a strength that, when the weight of the filtering tool 120 is less than the predetermined value, the filtering tool 120 is maintained in the first position. The urging force generated by the urging unit 23 is weaker than the gravity applied to the filtering tool 120 when the weight of the filtering tool 120 is greater than or equal to the predetermined value. Therefore, when the weight of the filtering tool 120 is greater than or equal to the predetermined value, the filtering tool 120 overcomes the urging force of the urging unit 23 and is positioned in the second position which is lower than the first position.

In the present embodiment, as an example, the urging unit 23 is configured with elastically deformable members. More specifically, the urging unit 23 of the present embodiment is a torsion coil spring configured to apply the urging force around the rotation axis A to the swinging unit 21. Note that the urging unit 23 may also be: other forms of spring, for example a coil spring, a leaf spring, and a torsion bar spring; rubber; and a synthetic resin.

The hindering unit 30 hinders removal of the filtering tool 120 from the holding unit 10, when the filtering tool 120 is attached to the holding unit 10 and the filtering tool 120 is positioned in the second position. The hindering unit 30 allows removal of the filtering tool 120 from the holding unit 10, when the filtering tool 120 is attached to the holding unit 10 and the filtering tool 120 is positioned in the first position.

A configuration of the hindering unit 30 hindering removal of the filtering tool 120 from the holding unit 10 is not particularly limited. As shown in FIG. 9, in the present embodiment, the hindering unit 30 is fixed to the base 2, and is arranged on a removal route through which the filtering tool 120 passes when the filtering tool 120 positioned in the second position is removed from the holding unit 10, as an example.

In other words, when the filtering tool 120 is attached to the holding unit 10 and the filtering tool 120 is positioned in the second position, the hindering unit 30 interferes with the filtering tool 120 to hinder movement of the filtering tool 120 in a direction away from the holding unit 10 along the axis E.

More specifically, the hindering unit 30 of the present embodiment is a convex portion 31 that protrudes from the base 2 over the removal route. The convex portion 31 is arranged below the filtering tool 120 positioned in the second position. When the filtering tool 120 is positioned in the second position, filtering tool 120 is arranged between the holding unit 10 and the convex portion 31.

Therefore, when the filtering tool 120 is positioned in the second position, even if the user applies a force to the filtering tool 120 in a direction of removal from the holding unit 10, the hindering unit 30 hinders the movement of the filtering tool 120, whereby the removal of the filtering tool 120 from the holding unit 10 is prevented.

When the filtering tool 120 is positioned in the first position, the hindering unit 30 retreats from the removal route as shown in FIG. 8. Therefore, when the filtering tool 120 is positioned in the first position, if the user applies a force to the filtering tool 120 in the direction of removal from the holding unit 10, the filtering tool 120 is removed from the holding unit 10.

As explained in the foregoing, the filtering tool holding device 1 includes the moving unit 20 configured to move the filtering tool 120 according to the change in the weight of the filtering tool 120 before and after carrying out the discharging operation of discharging the liquid inside the filtering tool 120. When the weight of the filtering tool 120 is greater than or equal to the predetermined value prior to carrying out the discharging operation, the filtering tool 120 is positioned in a position where removal from the holding unit 10 is hindered by the hindering unit 30.

In the case in which the endoscope reprocessor 1 includes the lever 3, the lever 3 and the moving unit 20 do not coordinate. Even when the lever 3 is lowered, the filtering tool 120 goes down along the axis E in the state of being positioned in the second position, whereby removal of the filtering tool 120 is hindered by the hindering unit 30.

The moving unit 20 is configured to move the filtering tool 120 downward when the weight of the filtering tool 120 is greater than or equal to the predetermined value, and therefore has a simple structure and can be manufactured inexpensively. The hindering unit 30 is also a member configured to interfere with the movement of the filtering tool 120, and therefore has a simple structure and can be manufactured inexpensively.

Therefore, the endoscope reprocessor 100 according to the present embodiment enables prevention of leakage of a liquid during removal of the filtering tool 120, by preventing removal of the filtering tool 120 by a convenient mechanism when the liquid is present in the filtering tool 120 in an amount greater than or equal to the predetermined amount, and can be manufactured inexpensively.

Figure 10:
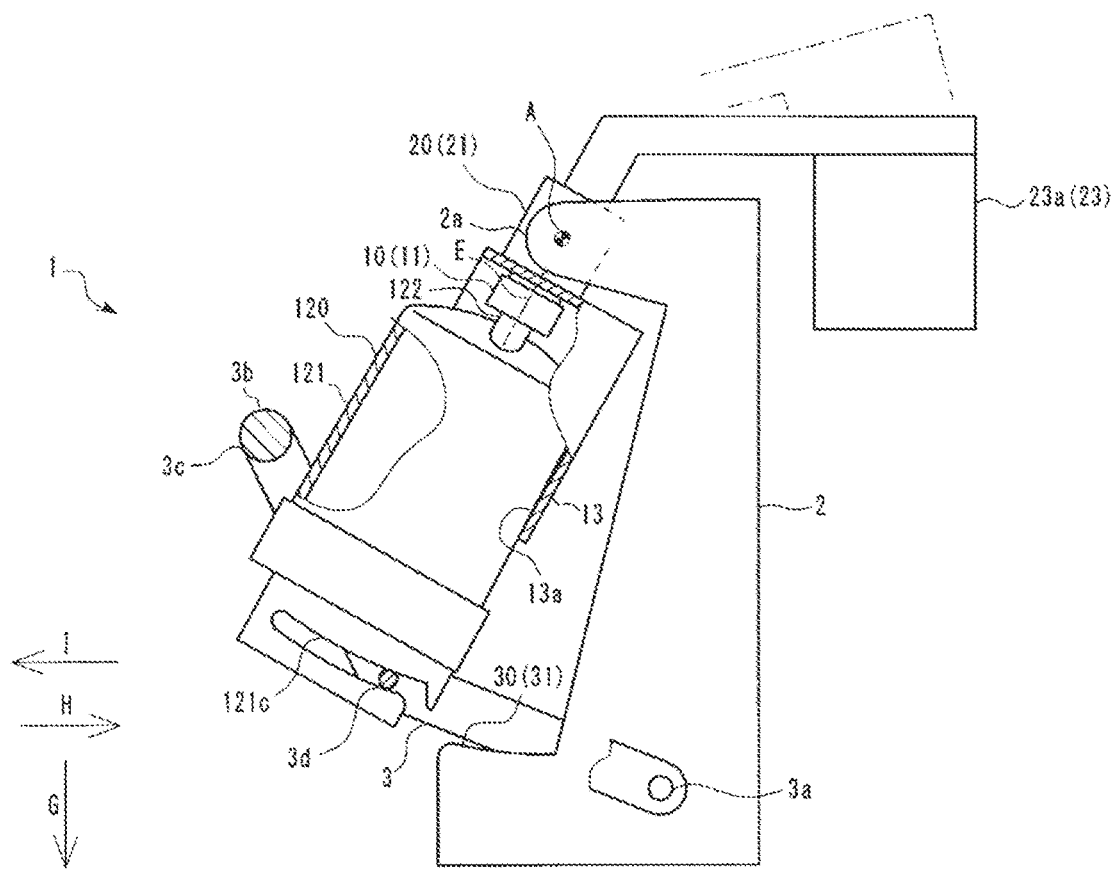
FIG. 10 shows a modification of the filtering tool holding device of the first embodiment.

FIG. 10 shows a modification of the present embodiment. In the present embodiment, the urging unit 23 generates an urging force by means of the elastically deformable member. However, the urging unit 23 is not limited to the configuration of using the elastically deformable member. The urging unit 23 in the filtering tool holding device 1 of the modification shown in FIG. 10 is provided with a weight 23a. By means of the weight of the weight 23a, the urging unit 23 generates the urging force moving the filtering tool 120 in the state of being attached to the holding unit 10 in a direction from the second position to the first position.

Second Embodiment

Hereinafter, the second embodiment of the present invention is described. In the following description, only differences from the first embodiment are explained, and constitutive elements similar to the constitutive elements of the first embodiment are denoted by the same reference symbols and description of the constitutive elements is omitted as appropriate.

In the first embodiment, the hindering unit 30 has a configuration of directly interfering with the filtering tool 120 to hinder removal of the filtering tool 120. However, the configuration of the hindering unit 30 is not limited to the configuration of the first embodiment.

Figure 11:
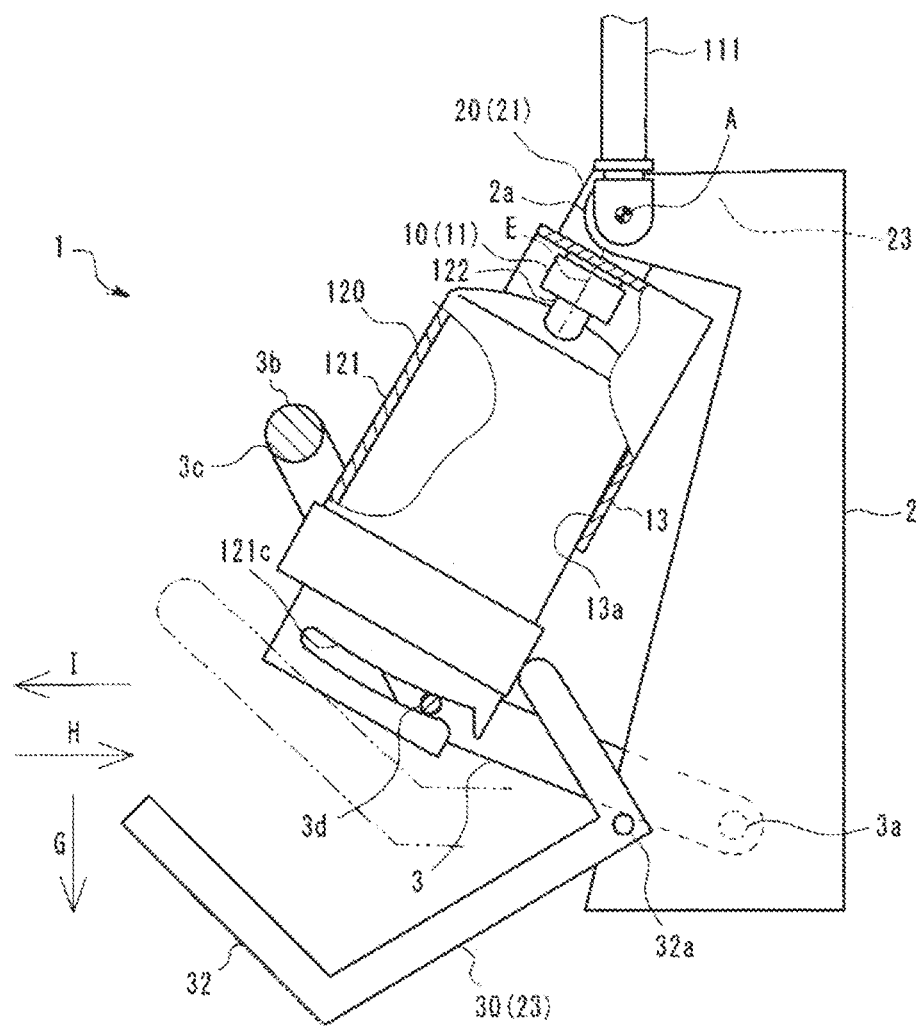
FIG. 11 is a lateral view of a filtering tool holding device of a second embodiment.
Figure 12:
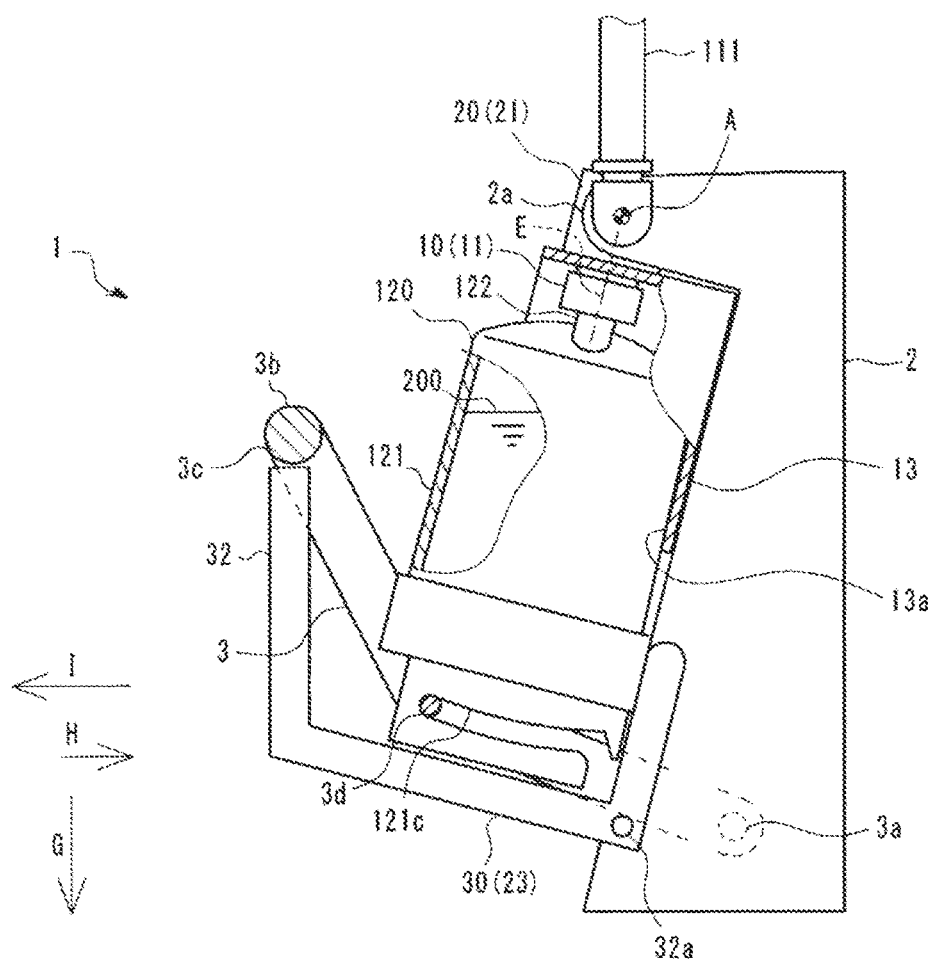
FIG. 12 is a lateral view of the filtering tool holding device of the second embodiment.

FIG. 11 and FIG. 12 show a configuration of the filtering tool holding device 1 according to the present embodiment. FIG. 11 shows the state in which the filtering tool 120 is positioned in the first position, and FIG. 12 shows the state in which the filtering tool 120 is positioned in the second position.

The filtering tool holding device 1 according to the present embodiment is different from the first embodiment in the configuration of the hindering unit 30. The hindering unit 30 of the present embodiment is configured to, when the filtering tool 120 is positioned in the second position, restrict movement of the lever 3 to hinder removal of the filtering tool 120 from the holding unit 10.

The hindering unit 30 of the present embodiment includes an arm portion 32 configured to swing around a pivot point 32a with respect to the base 2. As shown in FIG. 11, the arm portion 32 is largely spaced apart from the filtering tool 120 and the lever 3 downward when the filtering tool 120 is positioned in the first position.

The arm portion 32 rises up according to the movement of the filtering tool 120 from the first position to the second position. And then, when the filtering tool 120 is positioned in the second position, the arm portion 32 interferes with the lever 3 to restrict movement of the lever 3 as shown in FIG. 12. As described above, the lever 3 is a member that the user operates upon removal of the filtering tool 120 from the holding unit 10. Therefore, the hindering unit 30 hinders removal of the filtering tool 120 from the holding unit 10 when the filtering tool 120 is positioned in the second position.

Similarly to the first embodiment, the endoscope reprocessor 100 according to the present embodiment enables prevention of leakage of a liquid during removal of the filtering tool 120, by preventing removal of the filtering tool 120 when the liquid is present in the filtering tool 120 in an amount greater than or equal to the predetermined amount.

In the present embodiment, an urging force moving the filtering tool 120 in a direction from the second position to the first position is generated by means of the weight of the arm portion 32 configured to move according to movement of the filtering tool 120. In other words, in the present embodiment, the hindering unit 30 acts also as the urging unit 23.

Note that, in the present embodiment, the hindering unit 30 has a configuration of restricting the movement of the lever 3 when the filtering tool 120 is positioned in the second position. However, the hindering unit 30 may also be configured to cover over the grasping portion 3c of the lever 3 to hinder the user from touching the lever 3 when the filtering tool 120 is positioned in the second position.

Third Embodiment

Hereinafter, the third embodiment of the present invention is described. In the following description, only differences from the first embodiment are explained, and constitutive elements similar to the constitutive elements of the first embodiment are denoted by the same reference symbols and description of the constitutive elements is omitted as appropriate.

In the first embodiment, the moving unit 20 has a configuration of swinging the holding unit 10 and the filtering tool 120 around the rotation axis A with respect to the base 2 according to the weight of the filtering tool 120. However, the configuration of the moving unit 20 is not limited to the configuration of the first embodiment.

Figure 13:
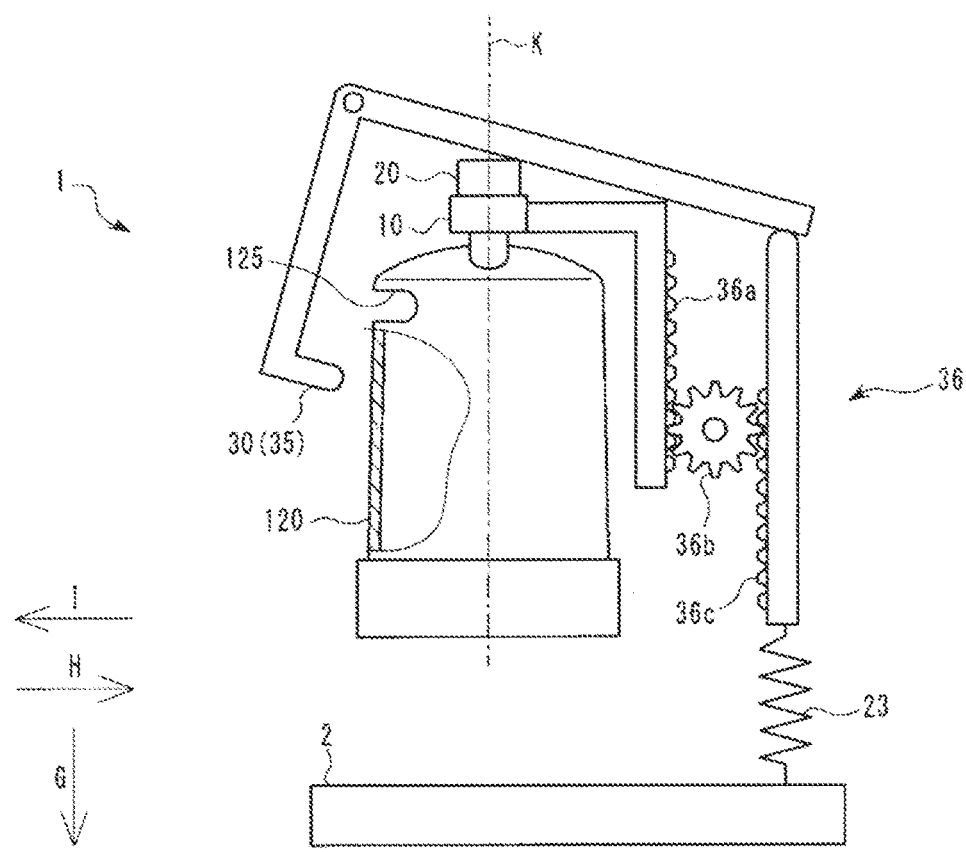
FIG. 13 is a lateral view of a filtering tool holding device of a third embodiment.
Figure 14:
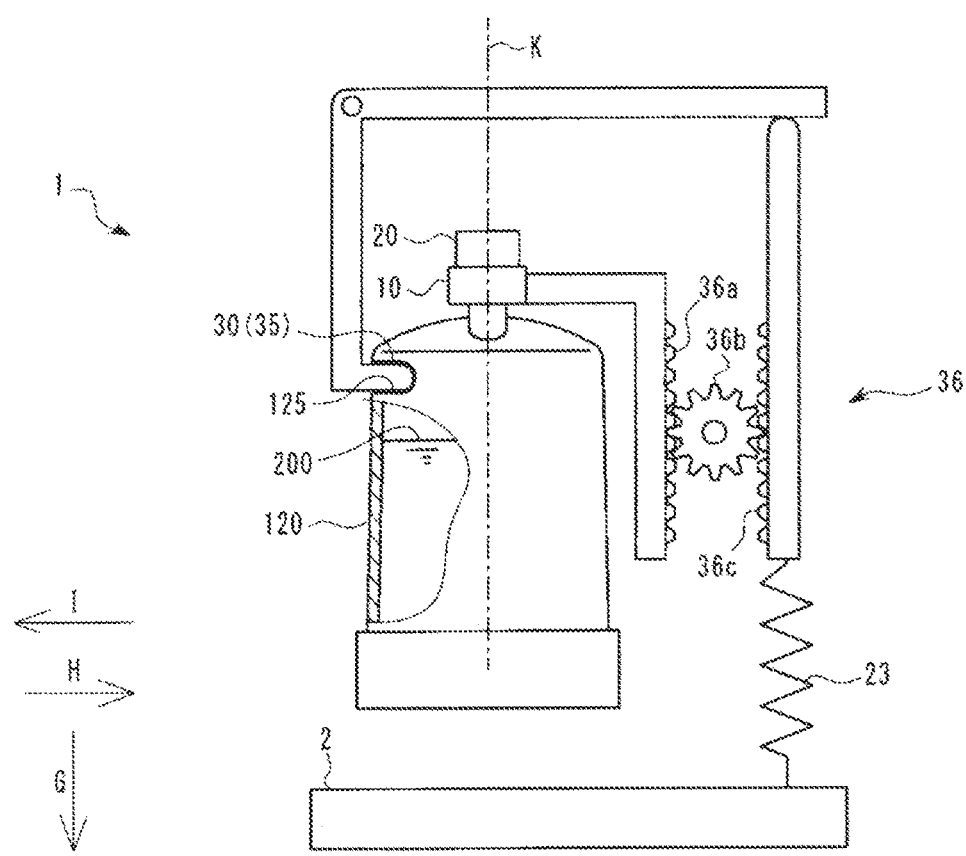
FIG. 14 is a lateral view of the filtering tool holding device of the third embodiment.

FIG. 13 and FIG. 14 show a configuration of the filtering tool holding device 1 according to the present embodiment. FIG. 13 shows the state in which the filtering tool 120 is positioned in the first position, and FIG. 14 shows the state in which the filtering tool 120 is positioned in the second position.

The moving unit 20 of the present embodiment advances and retreats the holding unit 10 and the filtering tool 120 along a predetermined linear axis K with respect to the base 2. As in the first embodiment, the second position is lower than the first position. Therefore, when the weight of the filtering tool 120 is less than the predetermined value, the filtering tool 120 is positioned in the first position as shown in FIG. 13. When the weight of the filtering tool 120 is greater than or equal to the predetermined value, the filtering tool 120 is positioned in the second position as shown in FIG. 14.

The hindering unit 30 of the present embodiment is provided with a lock mechanism 35 configured to operate according to movement of the holding unit 10 and the filtering tool 120. The lock mechanism 35 of the present embodiment illustrated in the figures fits into a fitting portion 125 formed on the filtering tool 120 when the filtering tool 120 is positioned in the second position.

In the present embodiment, as an example, the fitting portion 125 is a concave portion formed on an outer surface of the filtering tool 120. The lock mechanism 35 is provided with a convex portion configured to fit into the fitting portion 125. The lock mechanism 35 retreats from the fitting portion 125 when the filtering tool 120 is positioned in the first position. In the state in which the lock mechanism 35 fits into the fitting portion 125, the lock mechanism 35 prevents movement of the filtering tool 120 in the direction away from the holding unit 10. Note that the lock mechanism 35 may have a concave shape and the fitting portion 125 formed on the filtering tool 120 may have a convex shape.

In the present embodiment, a power transmission mechanism 36 configured to move the lock mechanism 35 according to movement of the holding unit 10 is provided with, as an example, a first rack gear 36a fixed on the holding unit 10, a pinion gear 36b engaging with the rack gear 36a, and a second rack gear 36c engaging with the pinion gear 36b. The pinion gear 36b is rotatably supported around a predetermined axis with respect to the base 2. The first rack gear 36a and the second rack gear 36c are enabled to advance and retreat with respect to the base 2 in parallel to the linear axis K. The power transmission mechanism 36 is provided with a link mechanism configured to transmit advancing and retreating movement of the second rack gear 36c to the lock mechanism 35.

Similarly to the first embodiment, the endoscope reprocessor 100 according to the present embodiment provided with the moving unit 20 and the hindering unit 30 of the aforementioned configurations enables prevention of leakage of a liquid during removal of the filtering tool 120, by preventing removal of the filtering tool 120 when the liquid is present in the filtering tool 120 in an amount greater than or equal to the predetermined amount.

Fourth Embodiment

Hereinafter, the fourth embodiment of the present invention is described. In the following description, only differences from the first embodiment are explained, and constitutive elements similar to the constitutive elements of the first embodiment are denoted by the same reference symbols and description of the constitutive elements is omitted as appropriate.

In the first embodiment, the moving unit 20 has a configuration of swinging the holding unit 10 and the filtering tool 120 around the rotation axis A with respect to the base 2 according to the weight of the filtering tool 120. However, the configuration of the moving unit 20 is not limited to the configuration of the first embodiment.

Figure 15:
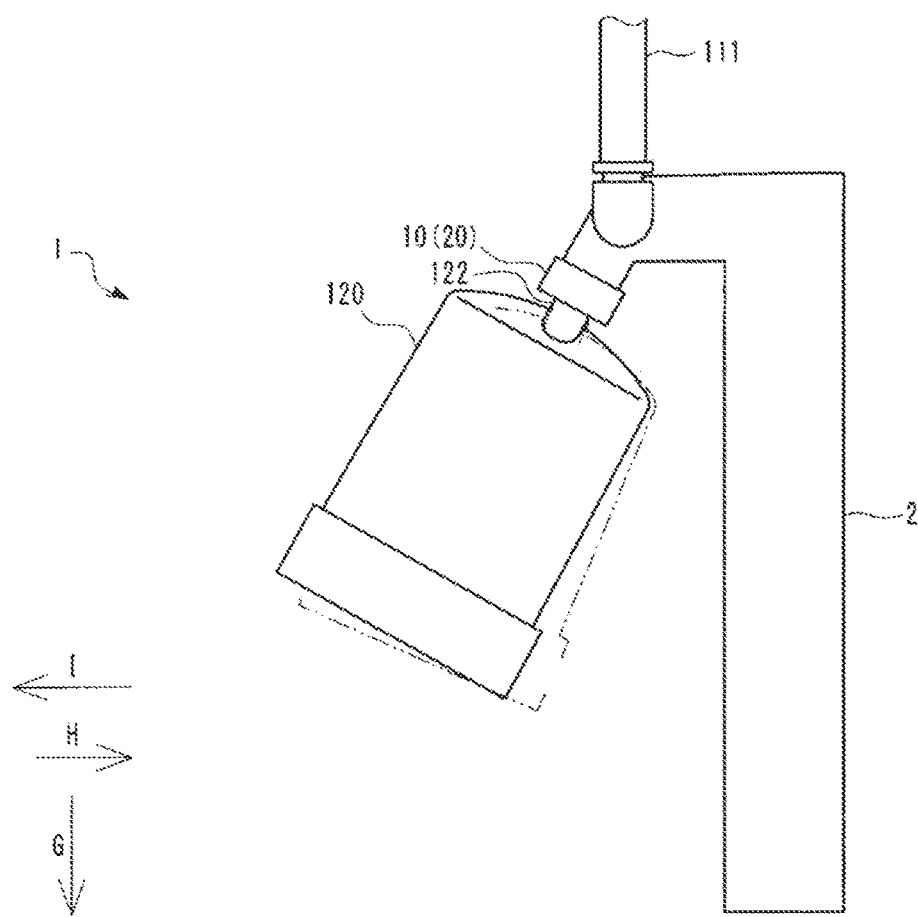
FIG. 15 is a lateral view of a filtering tool holding device of a fourth embodiment.

FIG. 15 shows a configuration of the filtering tool holding device 1 according to the present embodiment. In the present embodiment, the holding unit 10 is fixed to the base 2. The filtering tool 120 swings according to the weight in the state of being attached to the holding unit 10, with a joint part with the holding unit 10 as a pivot point.

Figure 16:
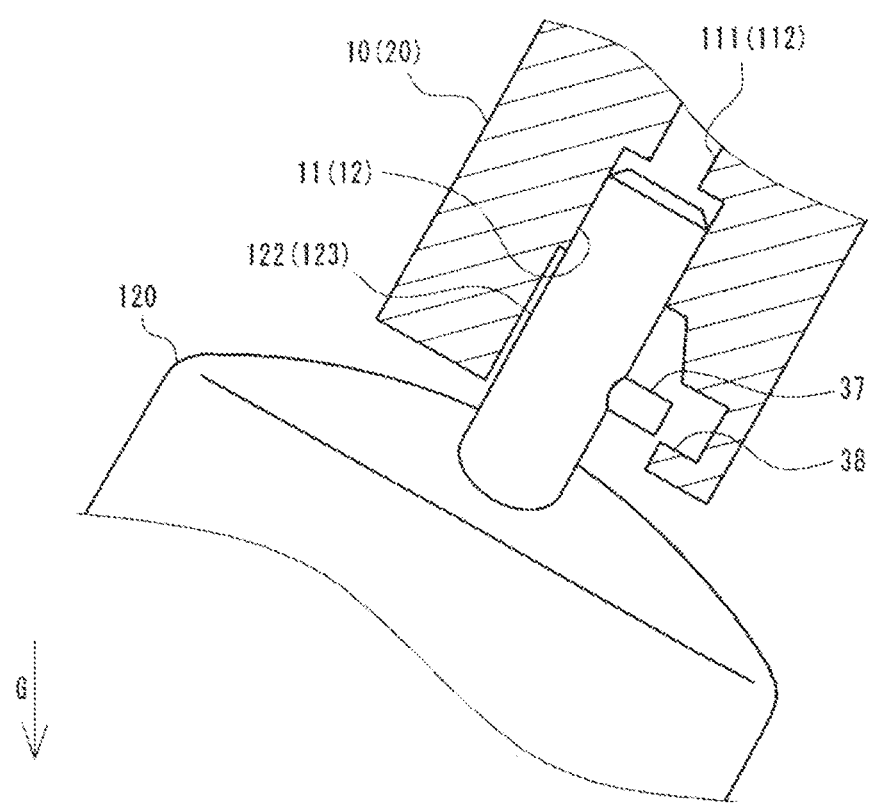
FIG. 16 is a cross-sectional view of a hindering unit of the fourth embodiment.
Figure 17:
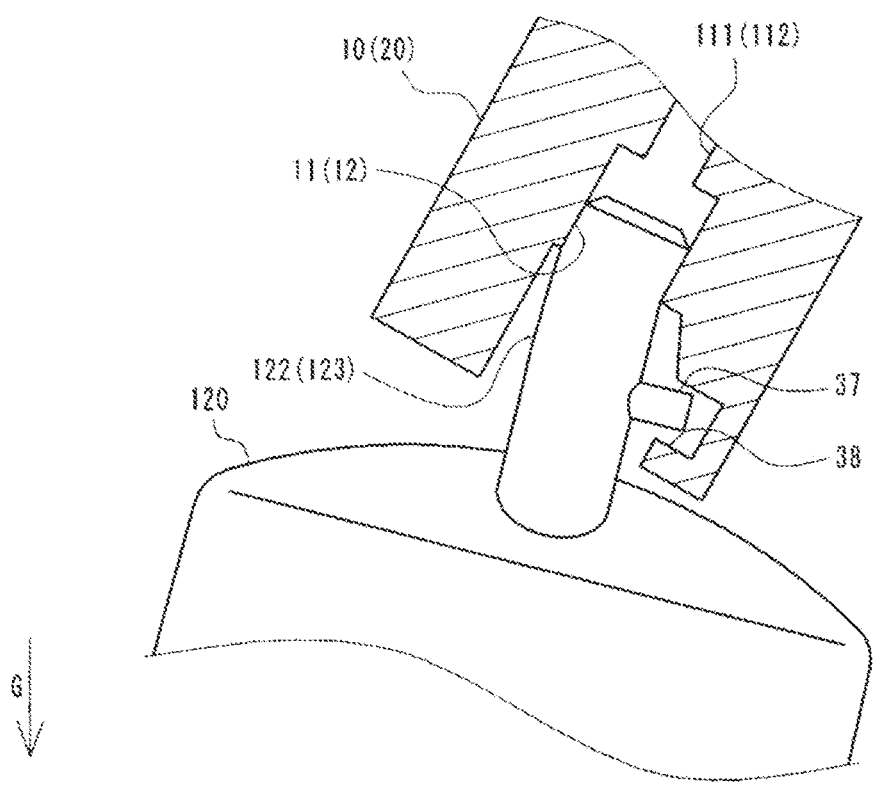
FIG. 17 is a cross-sectional view of the hindering unit of the fourth embodiment.

FIG. 16 and FIG. 17 are enlarged views of the joint part between the holding unit 10 and the filtering tool 120. FIG. 16 shows the state in which the filtering tool 120 is positioned in the first position, and FIG. 17 shows the case in which the filtering tool 120 is positioned in the second position.

There is a slight gap in the joint part between the holding unit 10 and the filtering tool 120, that is, between: the first socket 11 and the second socket 12; and the primary side plug 122 and the secondary side plug 123. The gap is sealed with a packing which is not illustrated. The first socket 11 and the second socket 12, and the primary side plug 122 and the secondary side plug 123, slightly deform elastically according to the change in the weight of the filtering tool 120. In the present embodiment, the filtering tool 120 moves up and down in the vertical direction with respect to the holding unit 10 according to the change in the weight, by an amount corresponding to the gap of the joint part between the holding unit 10 and the filtering tool 120 as well as the elastic deformation.

As shown in FIG. 16 and FIG. 17, the hindering unit 30 of the present embodiment is a concave portion 38 formed on inner peripheral faces of the first socket 11 and the second socket 12. The primary side plug 122 and the secondary side plug 123 are each provided with a fitting portion 37 protruding from a lateral face.

As shown in FIG. 17, the fitting portion 37 fits into the concave portion 38 when the filtering tool 120 is positioned in the second position. In the state in which the fitting portion 37 fits into the concave portion 38, movement of the primary side plug 122 and the secondary side plug 123 in a direction of uncoupling from the first socket 11 and the second socket 12 is restricted. As shown in FIG. 16, the fitting portion 37 retreats from the concave portion 38 when the filtering tool 120 is positioned in the first position.

Note that in the present embodiment, the hindering unit 30 formed on the inner peripheral faces of the first socket 11 and the second socket 12 may have a convex shape, and the fitting portion 37 formed on the primary side plug 122 and the secondary side plug 123 may have a concave shape.

Similarly to the first embodiment, the endoscope reprocessor 100 according to the present embodiment provided with the hindering unit 30 of the aforementioned configuration enables prevention of leakage of a liquid during removal of the filtering tool 120, by preventing removal of the filtering tool 120 when the liquid is present in the filtering tool 120 in an amount greater than or equal to the predetermined amount.

Fifth Embodiment

Hereinafter, the fifth embodiment of the present invention is described. In the following description, only differences from the first embodiment are explained, and constitutive elements similar to the constitutive elements of the first embodiment are denoted by the same reference symbols and description of the constitutive elements is omitted as appropriate.

Figure 18:
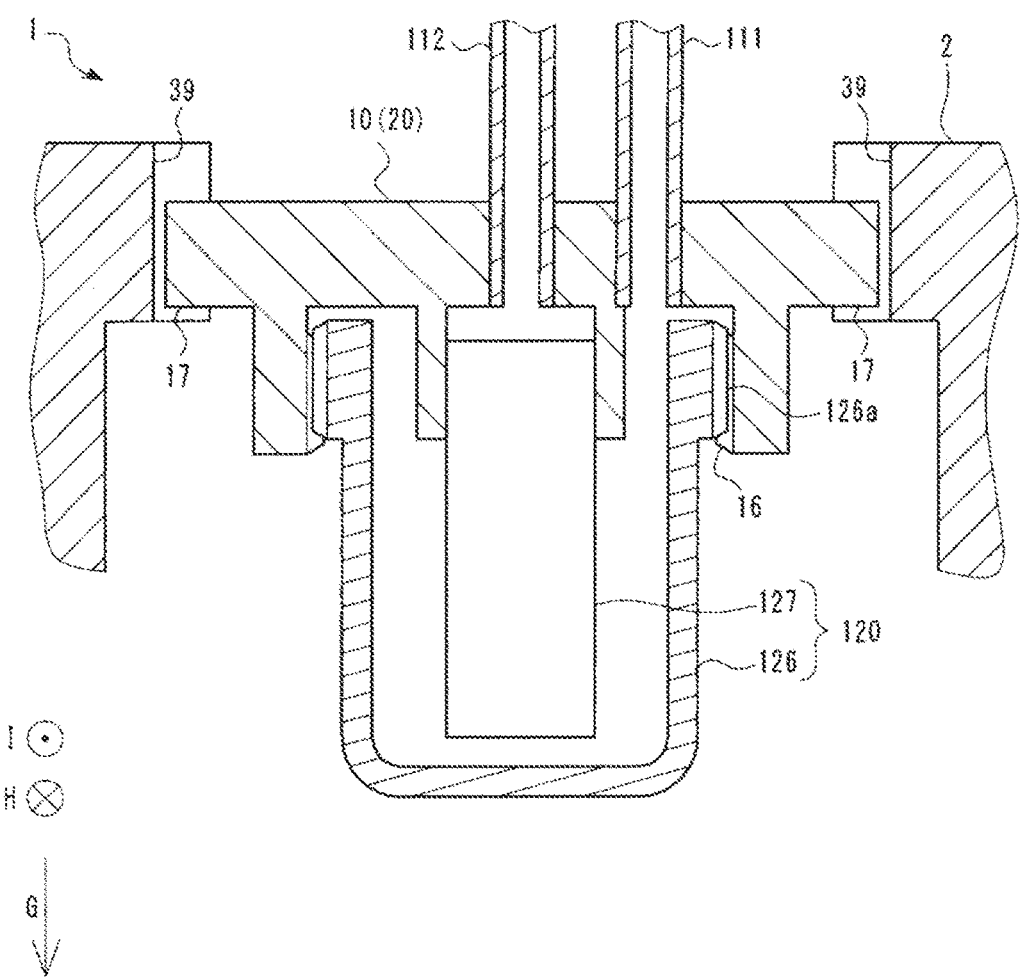
FIG. 18 is a front view of a filtering tool holding device of a fifth embodiment.
Figure 19:
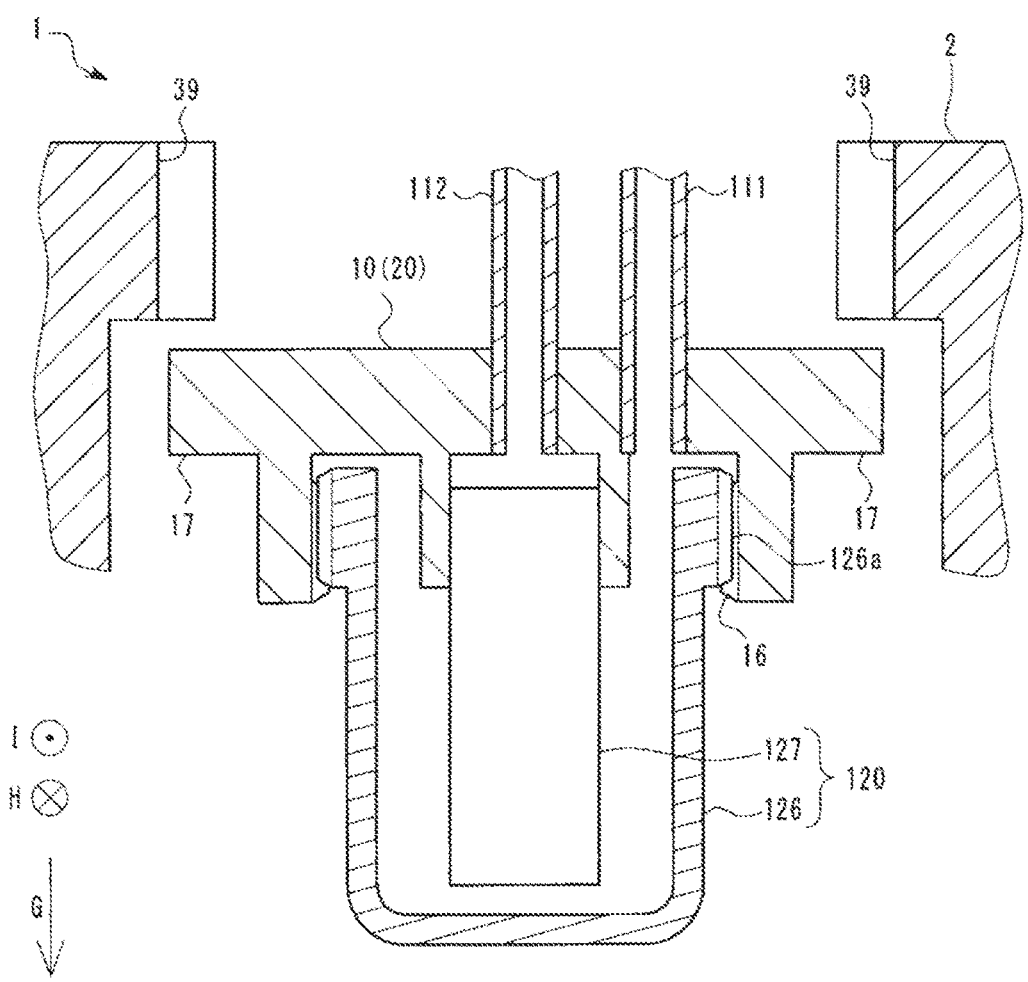
FIG. 19 is a front view of the filtering tool holding device of the fifth embodiment.
Figure 20:
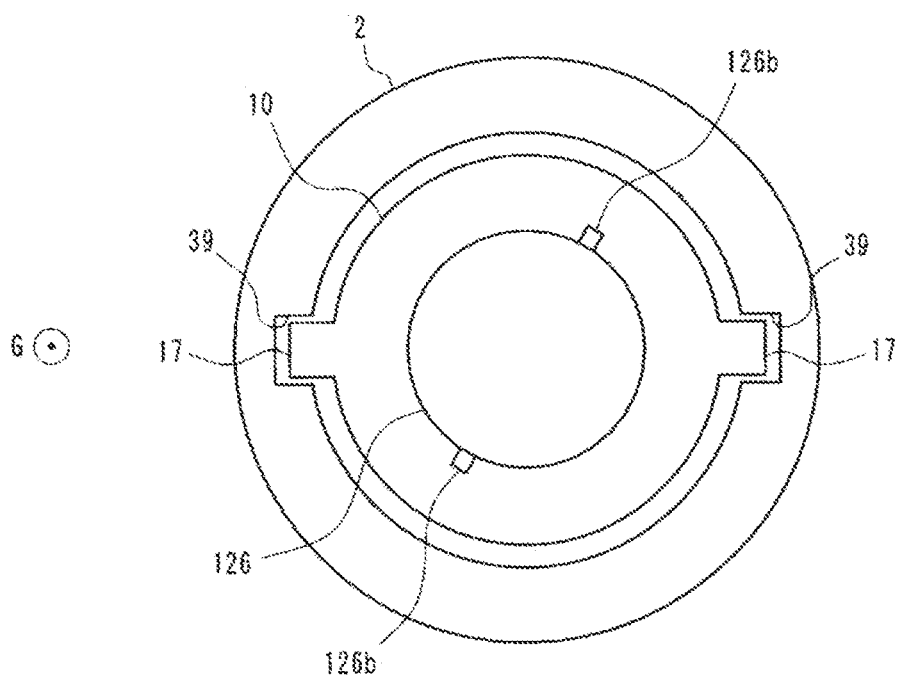
FIG. 20 shows the filtering tool holding device of the fifth embodiment viewed from below.

FIG. 18 and FIG. 19 are cross-sectional views of the filtering tool holding device 1 according to the present embodiment. FIG. 18 shows the state in which the filtering tool 120 is positioned in the first position, and FIG. 19 shows the state in which the filtering tool 120 is positioned in the second position. FIG. 20 shows the filtering tool holding device 1 viewed from below.

The filtering tool 120 of the present embodiment includes a housing 126 and a filter 127 attachable and detachable to/from the holding unit 10. The housing 126 is a member having a bottomed cylindrical shape. A male thread 126a is formed on an outer periphery of an opening portion of the housing 126. The male thread 126a is screwed with a female thread 16 provided on a lower face of the holding unit 10. In the present embodiment, a central axis of the female thread 16 is substantially perpendicular.

In the state in which the housing 126 is attached to the holding unit 10, the holding unit 10 acts as a lid sealing the opening portion of the housing 126. The filter 127 is, in the state of being attached to the holding unit 10, arranged in a space surrounded by the housing 126 and the holding unit 10.

The fluid introduction conduit 111 and the fluid discharge conduit 112 are connected to the holding unit 10. The fluid introduction conduit 111 communicates with a primary side space of the filter 127 in the space surrounded by the housing 126 and the holding unit 10. The fluid discharge conduit 112 communicates with a secondary side space of the filter 127 in the space surrounded by the housing 126 and the holding unit 10.

In the present embodiment, when replacing the filter 127, the user carries out the discharge operation of discharging the liquid inside the housing 126 and then removes the housing 126 from the holding unit 10 to expose the filter 127 to the outside. Thereafter, the user removes the filter 127 from the holding unit 10. In order to remove the housing 126 from the holding unit 10, it is required to apply torque for rotating around an axis perpendicular to the holding unit 10 to the housing 126, by using a tool which is not illustrated.

FIG. 20 shows the filtering tool holding device 1 viewed from below. On the outer peripheral face of the housing 126, a projection 126b is provided with which the tool is engaged when an operation of rotating the housing 126 with respect to the holding unit 10 is carried out.

The holding unit 10 moves up and down in the vertical direction according to the change in the weight of the filtering tool 120 as shown in FIG. 18 and FIG. 19. In other words, the holding unit 10 acts also as the moving unit 20. When the weight of the filtering tool 120 is less than the predetermined value, the holding unit 10 is positioned in the first position with the filtering tool 120 as shown in FIG. 18. On the other hand, when the weight of the filtering tool 120 is greater than or equal to the predetermined value, the holding unit 10 is positioned in the second position which is lower than the first position, as shown in FIG. 19.

The holding unit 10 has a disk shape as shown in FIG. 20. A plurality of convex portions 17 protruding outwards in a radial direction are provided on the outer peripheral face of the holding unit 10. As shown in FIG. 18, the convex portions 17 engage with the concave portions 39 provided on the base 2 when the filtering tool 120 and the holding unit 10 are positioned in the first position. As shown in FIG. 19, the convex portions 17 retreat from the concave portions 39 provided on the base 2 when the filtering tool 120 and the holding unit 10 are positioned in the second position.

In the state in which the convex portions 17 engage with the concave portions 39, the holding unit 10 is restricted from rotating around the axis perpendicular to the base 2. On the other hand, in the state in which the convex portions 17 retreat from the concave portions 39, the holding unit 10 is rotatable around the axis perpendicular to the base 2.

In the case in which the holding unit 10 is restricted from rotating around the axis perpendicular to the base 2, the housing 126 can be rotated with respect to the holding unit 10 when the torque around the perpendicular axis is applied to the housing 126. In such a case, the housing 126 can be removed from the holding unit 10.

In the case in which the holding unit 10 is rotatable around the axis perpendicular to the base 2, the holding unit 10 is rotated around the perpendicular axis together with the housing 126 when the torque around the perpendicular axis is applied to the housing 126. In such a case, the housing 126 cannot be removed from the holding unit 10. In other words, the hindering unit 30 of the present embodiment releases the engagement between the convex portions 17 provided on the holding unit 10 and the concave portions 39 provided on the base 2, to hinder removal of the filtering tool 120 from the holding unit 10.

Similarly to the first embodiment, the endoscope reprocessor 100 according to the present embodiment provided with the hindering unit 30 of the aforementioned configuration enables prevention of leakage of a liquid during removal of the filtering tool 120, by preventing removal of the filtering tool 120 when the liquid is present in the filtering tool 120 in an amount greater than or equal to the predetermined amount.

The present invention is not limited to the aforementioned embodiments and can be modified as appropriate without departing from the gist or idea of the present invention that can be read from the Claims and the Specification as a whole. An endoscope reprocessor with such a modification is also encompassed in the technical scope of the present invention.

What is claimed is:

1. An endoscope reprocessor comprising:
   a holding member to/from which a filtering tool is attachable and detachable;
   a fluid introduction conduit and a fluid discharge conduit that communicate with the filtering tool in a state in which the filtering tool is attached to the holding member;
   a moving member configured to, when the filtering tool is attached to the holding member and a weight of the filtering tool is less than a predetermined value, position the filtering tool in a first position and, when the filtering tool is attached to the holding member and the weight of the filtering tool is greater than or equal to the predetermined value, position the filtering tool in a second position that is different from the first position; and
   a hindering unit configured to, when the filtering tool is positioned in the second position, hinder removal of the filtering tool from the holding member.

2. The endoscope reprocessor according to claim 1, wherein the moving member comprises a swinging member configured to swing the holding member and the filtering tool around a rotation axis in a state in which the filtering tool is attached to the holding member.

3. The endoscope reprocessor according to claim 1, wherein the hindering unit is positioned on a removal route through which the filtering tool passes during removal of the filtering tool from the holding member when the filtering tool is positioned in the second position.

4. The endoscope reprocessor according to claim 1, further comprising the filtering tool, wherein
the filtering tool comprises a fitting portion that fits into the hindering unit when the filtering tool is attached to the holding member and in the second position.

5. An endoscope reprocessor comprising:
a holding member to/from which a filtering tool is attachable and detachable;
a fluid introduction conduit and a fluid discharge conduit that communicate with the filtering tool in a state in which the filtering tool is attached to the holding member;
a moving member configured to, when the filtering tool is attached to the holding member and a liquid is present in an amount less than a predetermined amount in the filtering tool, position the filtering tool in a first position and, when the filtering tool is attached to the holding member and the liquid is present in an amount greater than or equal to the predetermined amount in the filtering tool, position the filtering tool in a second position that is different from the first position; and
a hindering unit configured to, when the filtering tool is positioned in the second position, hinder removal of the filtering tool from the holding member.

* * * * *